(12) United States Patent
Lu et al.

(10) Patent No.: US 7,711,447 B2
(45) Date of Patent: May 4, 2010

(54) SYSTEM AND METHOD FOR AUTOMATED GENERATING OF A CUTTING CURVE ON A SURFACE

(75) Inventors: Qinghui Peter Lu, San Jose, CA (US); Dmitry Sultanov, Moscow (RU); Pavel Agapov, Moscow (RU); Artem Borovinsklh, Moscow (RU); Maneesh Dhagat, San Jose, CA (US); Craig E. Farren, Livermore, CA (US); James C. Culp, Pleasanton, CA (US)

(73) Assignee: Align Technology, Inc., Santa Clara, CA (US)

( * ) Notice: Subject to any disclaimer, the term of this patent is extended or adjusted under 35 U.S.C. 154(b) by 671 days.

(21) Appl. No.: 11/551,395

(22) Filed: Oct. 20, 2006

(65) Prior Publication Data

US 2008/0187887 A1    Aug. 7, 2008

(51) Int. Cl.
*G06F 19/00* (2006.01)
*A61C 13/00* (2006.01)

(52) U.S. Cl. .................. 700/187; 700/178; 700/118; 433/24; 433/215

(58) Field of Classification Search .............. 700/187, 700/98, 117, 118, 178; 433/6, 24, 215
See application file for complete search history.

(56) References Cited

U.S. PATENT DOCUMENTS

| 6,371,761 | B1 | 4/2002 | Cheang et al. | |
|---|---|---|---|---|
| 6,386,878 | B1 | 5/2002 | Pavlovskaia et al. | |
| 6,409,504 | B1 | 6/2002 | Jones et al. | |
| 6,514,074 | B1 | 2/2003 | Chishti et al. | |
| 6,688,886 | B2 | 2/2004 | Hughes et al. | |
| 7,040,896 | B2 | 5/2006 | Pavlovskaia et al. | |
| 2006/0093982 | A1* | 5/2006 | Wen | 433/6 |
| 2006/0127859 | A1 | 6/2006 | Wen | |
| 2008/0131846 | A1* | 6/2008 | Marshall et al. | 433/218 |
| 2008/0254402 | A1* | 10/2008 | Hilliard | 433/24 |

OTHER PUBLICATIONS

International Search Report from European Patent Office dated Oct. 29, 2009 for International Application No. PCT/US2007/081988.
Written Opinion from European Patent Office dated Oct. 29, 2009 for International Application No. PCT.US2007/081988.

* cited by examiner

*Primary Examiner*—Ramesh B Patel
*Assistant Examiner*—Steven R Garland
(74) *Attorney, Agent, or Firm*—Klein, O'Neill & Singh, LLP

(57) ABSTRACT

In accordance with various aspects of the present invention, a system and method for automated generating of a cutting curve on a surface is provided. In accordance with an exemplary embodiment, a computer-implemented method for automated generating of a cutting curve on a gingival surface to facilitate cutting of an aligner material comprises the defining of initial gingival curves along the line around a tooth (LAT) on a patient's teeth, including within an interproximal area between teeth. The initial gingival curves are replaced with a modified, dynamic cutting curve comprising an offset adjustment configured to minimize weakening of a region of the aligner material within the interproximal area. This process for generating a modified, dynamic cutting curve within an interproximal area can be suitably applied or continued for each of other the teeth and interproximal areas between those teeth to define a complete dynamic cutting curve. The resulting complete dynamic cutting curve can then be output for conversion into machine executable code to facilitate cutting of the aligner material.

24 Claims, 14 Drawing Sheets

THE CORRECTION OF THE CUTTING TOOL POSITION AT THE COLLISION AREA

SYSTEM AND METHOD FOR AUTOMATED GENERATING OF A CUTTING CURVE ON A SURFACE

TECHNICAL FIELD

The present invention relates, generally, to mass customization of form fitting objects, and in particular to a system and method for automated generating of a cutting curve on a surface, such as for the generation of a cutting curve on a gingival surface to facilitate the cutting of an aligner material used in orthodontic treatment.

BACKGROUND OF THE INVENTION

The use of plastics or other materials to create form fitting objects requires precise development and manufacturing processes. Common form fitting objects typically include medical products like hearing aids, prosthetics or clear aligners for repositioning teeth.

The use of clear, plastic-type aligners for the re-positioning of teeth is becoming increasingly popular. Such aligners are typically produced by forming a plastic material over stereolithography (SLA) molds that represent various stages of treatment of a patient's orthodontic treatment. After forming the aligner material over a mold, the cutting of the aligner material occurs on the gingival surface along the interproximal area, i.e., a region that is proximate the gingival surface between the teeth and gums, to define the plastic aligner from the SLA molds. Conventional methodologies for creating such a cutting curve have various drawbacks.

For example, in many instances, the cutting curve has too many straight lines between the interproximal areas, with such straight line portions unable to provide sufficient resistance force to effectively facilitate teeth movement, and potentially cutting into the gingival surface of the patient and causing great pain. In other interproximal areas, a sharp shaped portion of the aligner material can result in stress risers, potentially causing the aligner material to break during treatment.

Manual trimming of the aligner material is also required in many instances, such as the punctured inner shell. As another example, in some cases the interproximal areas can have the cutting curve passing inside the jaw mold that leads to puncturing of the stereolithography (SLA) mold, requiring the SLA mold to be rebuilt and manually trimmed. Manual trimming is also typically required with such conventional processes in treating pontic cases, often requiring pontic cases to be filtered out from automation trimming line before such manual trimming, as well as in the back molar region to address extraneous material produced.

Still further, conventional techniques for generating cutting curves do not suitably address the potential for collisions of a cutting tool within the cutting machine when cutting the aligner material from the SLA molds.

SUMMARY OF THE INVENTION

In accordance with various aspects of the present invention, a system and method for automated generating of a cutting curve on a surface is provided. In accordance with an exemplary embodiment, a computer-implemented method for automated generating of a cutting curve on the surface to facilitate cutting of a material, e.g., for a form-fitting object, comprises defining initial surface curves along the line around the object, replacing the initially defined surface curves with a modified, dynamic curve, and then outputting a complete dynamic curve to facilitate cutting of the material for the form-fitting object.

In accordance with another exemplary embodiment, a computer-implemented method for automated generating of a cutting curve on a gingival surface to facilitate cutting of an aligner material comprises the defining of initial gingival curves along the line around a tooth (LAT) on a patient's jaw. The initial gingival curves are replaced with a modified, dynamic cutting curve, with the resulting complete dynamic cutting curve then output for conversion into machine executable code to facilitate cutting of the aligner material.

In accordance with other exemplary embodiments, the computer-implemented method for automated generating of a cutting curve on the gingival surface can also be configured to modify the dynamic cutting curve in a back molar region to remove extraneous material and/or to define a cutting curve region around a pontic object between two teeth.

In accordance with another exemplary embodiment of the present invention, to avoid collision of a cutting tool with teeth, attachment, inner shell and a fixture when cutting the aligner material, a computer-implemented method can also be provided to suitably define cutting angles and otherwise adjust the cutting tool along the dynamic cutting curve to provide a method for dynamic adjustment of the cutting tool.

BRIEF DESCRIPTION OF THE DRAWINGS

The exemplary embodiments of the present invention will be described in connection with the appended drawing figures in which like numerals denote like elements, and wherein.

DETAILED DESCRIPTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic, dental, medical or other treatment or therapeutic contexts, and/or any protective equipment or athletic applications, and the exemplary embodiments relating to a system and method for automated generating of a cutting curve on the gingival surface, and/or the control of a cutting tool to avoid collision, as described herein are merely a few of the exemplary applications for the invention. For example, the principles, features and methods discussed may be applied to any application or process in which the automated generation of a curve to facilitate the cutting or other separation of materials is conducted, or in which the cutting of such materials during the manufacture of devices and equipment can be suitably utilized, such as in the generation, design and/or manufacture of any form-fitting device. e.g., eye glass frames, contact or glass lens, hearing aids or plugs, artificial knee caps, prosthetic limbs and devices, orthopedic inserts, as well as protective equipment such as knee guards, athletic cups, or elbow, chin, and shin guard and other like athletic/protective devices.

Figure 1A:
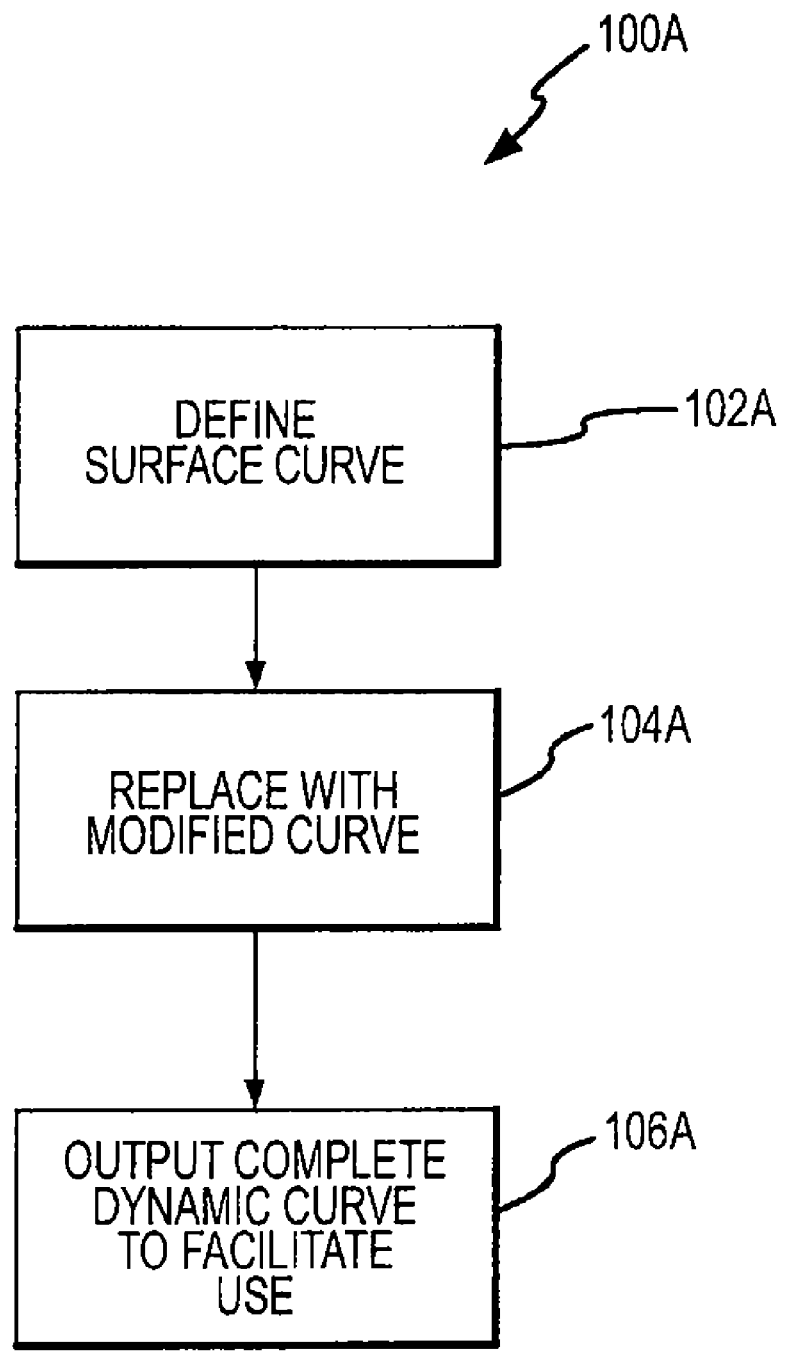
FIG. 1A illustrates a diagram of an exemplary method for automated generating of a cutting curve on a surface in accordance with an exemplary embodiment of the present invention.

In accordance with various aspects of the present invention, a system and method for automated generating of a cutting curve on a surface is provided. In accordance with an exemplary embodiment, with reference to FIG. 1A, a computer-implemented method 100A for automated generating of a cutting curve on the surface to facilitate cutting of a material, e.g., for a form-fitting object, comprises defining initial surface curves along the line around the object, such as within interproximal areas between two surfaces (102A), replacing the initially defined surface curves with a modified, dynamic curve (104B), and then outputting a complete dynamic curve to facilitate cutting of the material for the form-fitting object (106B). Such a method can be utilized in the field of form-fitting and other like devices to suitably cut plastics and other materials in manufacturing the device.

For example, in the design and manufacture of form-fitting objects such as eye glasses, method 100A can define initial surface curves around the nose-region of the eye glass frames (102A), e.g., along the lines of the eye glass frames around the upper nose surface, and then replace those initial surface curves using the processes disclosed herein to provide a modified, dynamic curve (104A). Such a modified, dynamic curve can then used suitably provided in an appropriate format to facilitate the cutting of the eye glass frames from composite materials, plastics or other suitably materials for eye glass frames. Similarly, when form-fitting an ear piece to be used, for example, as a hearing aid, audio ear piece, or noise reduction plugs, method 100A can define initial surface curves of the inner ear (102A), and then replace those initial surface curves using the processes disclosed herein to provide a modified, dynamic curve (104A). Such a dynamic curve can be provided in an appropriate format to facilitate the cutting of the form fitting ear piece from a desirable material.

Figure 1B:
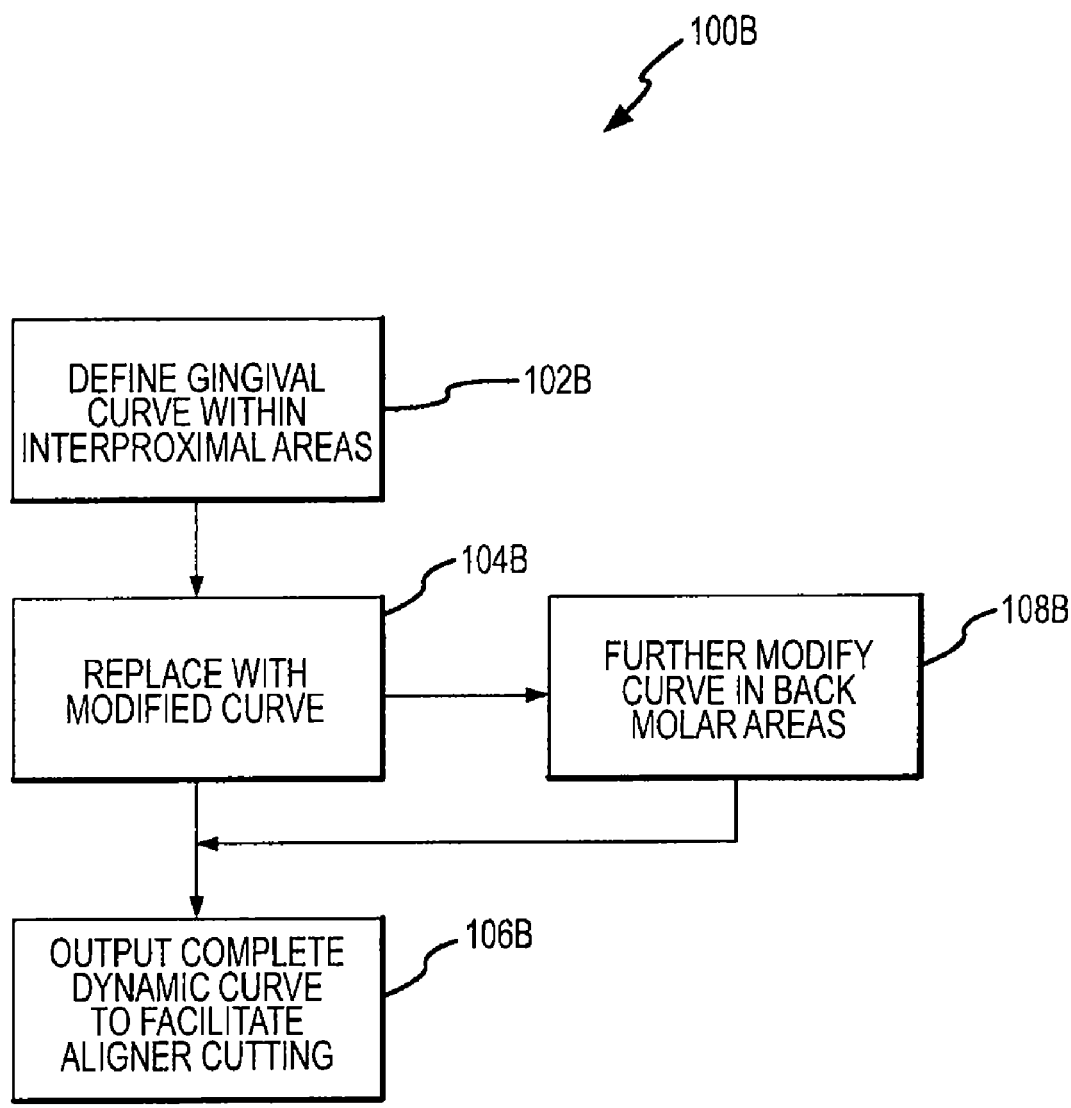
FIG. 1B illustrates a diagram of an exemplary method for automated generating of a cutting curve on a gingival surface in accordance with another exemplary embodiment of the present invention.

In accordance with an exemplary embodiment, with reference to FIG. 1B and the application to a gingival surface, a computer-implemented method 100B for automated generating of a cutting curve on the gingival surface to facilitate cutting of an aligner material comprises defining initial gingival curves along the line around a tooth (LAT) of a patient's jaw, including within interproximal areas between two teeth of a patient (102B), replacing the initially defined gingival curves with a modified, dynamic curve (104B), and then outputting a complete dynamic curve to facilitate aligner cutting (106B).

Defining the initial gingival curves along a line around a tooth (LAT) on a jaw within an interproximal area between two teeth (102B) can be suitably conducted by various conventional processes for providing a gingival curve along the LAT. For example, such generation of gingival curves can comprise any conventional computational orthodontics methodology or process for identification of gingival curves, now known or hereinafter derived. For example, the methodologies and processes for identification of gingival curves can include those disclosed in U.S. Pat. No. 7,040,896, entitled "Systems and Methods for Removing Gingiva From Computer Tooth Models", and assigned to Align Technology, Inc. (the "'896 Patent") and U.S. Pat. No. 6,514,074, entitled "Digitally Modeling the Deformation of Gingival", and assigned to Align Technology, Inc. (the "'074 Patent"), and the various patents disclosed in the '896 and '074 Patents. In the '896 Patent, for example, such a process for identification of gingival curves can comprise a computer-implemented method separates a tooth from an adjacent structure, such as a gingiva, by defining a cutting surface, and applying the cutting surface between the tooth and the structure to separate the tooth in a single cut. In the '074 Patent, for example, such a process for identification of gingival curves can comprise having a computer obtain a digital model of a patient's dentition, including a dental model representing the patient's teeth at a set of initial positions and a gingival model representing gum tissue surrounding the teeth, wherein the computer then derives from the digital model an expected deformation of the gum tissue as the teeth move from the initial positions to another set of positions.

In such processes, to obtain a digital model used to generate the gingival curves, a digital data set representing a tooth arrangement can be obtained, referred to as the IDDS. Such an IDDS may be obtained in a variety of ways. For example, the patient's teeth may be scanned or imaged using well known technology, such as X-rays, three-dimensional x-rays, computer-aided tomographic images or data sets, magnetic resonance images, etc. Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Pa., 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set. General techniques for producing plaster casts of teeth and generating digital models using laser scanning techniques are also described, for example, in U.S. Pat. No. 5,605,459.

Figure 2A:
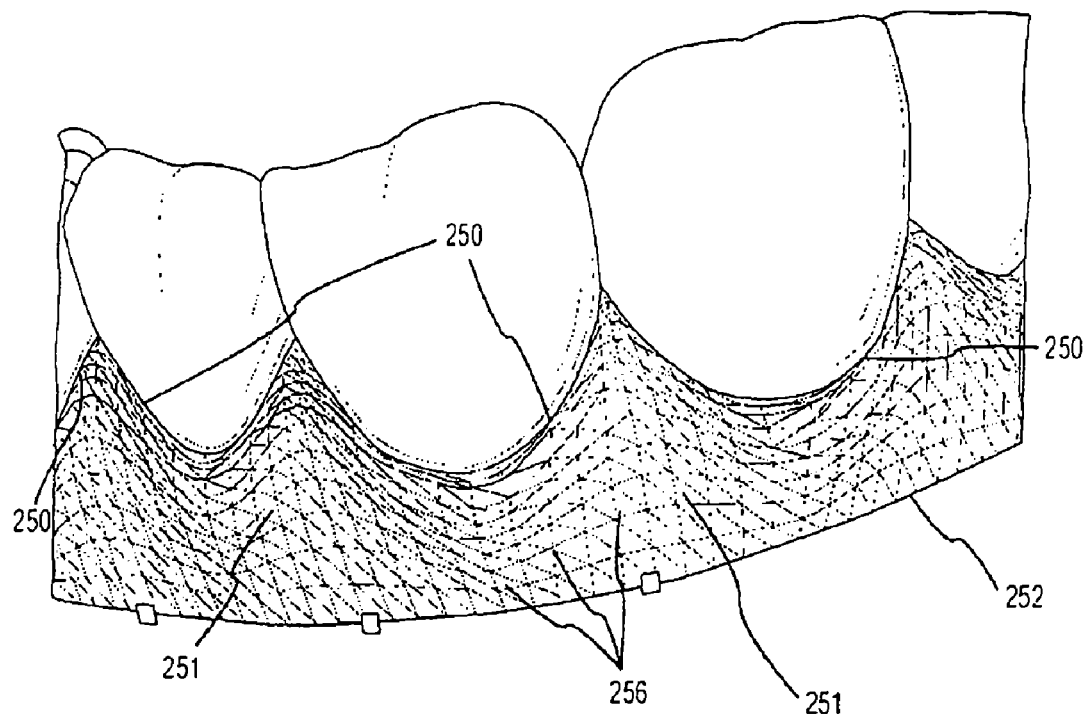
FIG. 2A illustrates diagram of an exemplary gingival surface and gingival parametric curves in accordance with an exemplary embodiment of the present invention.
Figure 2B:
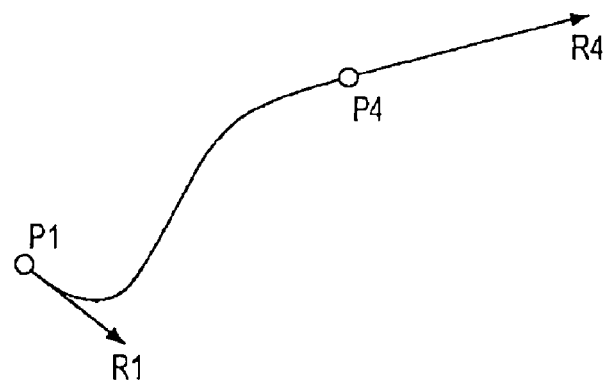
FIG. 2B illustrates a diagram of an Hermite-Spline curve in accordance with an exemplary embodiment of the present invention.
Figure 2C:
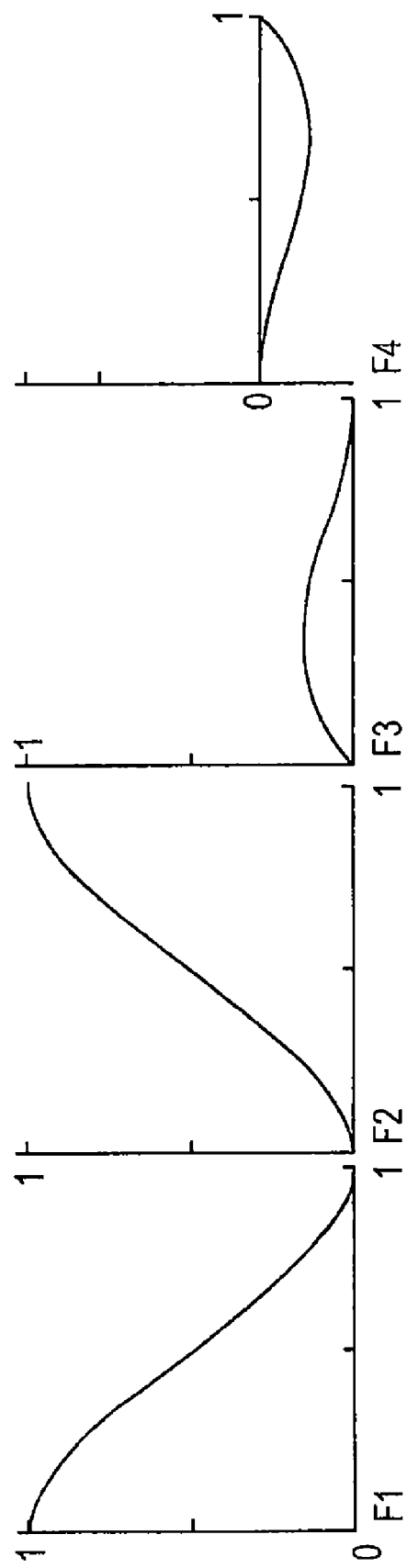
FIG. 2C illustrates a diagram of Hermite basic functions in accordance with an exemplary embodiment of the present invention.

In accordance with an exemplary embodiment, with reference to FIGS. 2A-2C, the initial gingival curves 250 can be generated by use of the conventional Hermite-Spline process. In general, the Hermite form of the cubic polynomial curve segment is determined by constraints on the endpoints $P_1$ and $P_4$ and tangent vectors at the endpoints $R_1$ and $R_4$. The Hermit curve can be written in the following form:

$$Q(s)=(2s^3-3s^2+1)P_1+(-2s^3+3s^2)P_4+(s^3-2s^2+s)R_1+(s^3-s^2)R_4; s[0,1] \quad (1)$$

Equation (1) can be rewritten as:

$$Q(s)=F_1(s)P_1+F_2(s)P_4+F_3(s)R_1+F_4(s)R_4; \quad (2)$$

Wherein equation (2) is the geometric form of Hermite-Spline Curve, the vectors $P_1, P_4, R_1, R_4$ are the geometric coefficients, and the F terms are Hermit basis functions. FIG. 2B shows a Hermite-Spline defined by $P_1, P_4, R_1, R_4$, and FIG. 2C shows four Hermite basis functions.

With reference to FIG. 2A, a gingival surface 251 comprises a set of gingival parametric curves 256. A gingival surface 251 is defined by gingival curves 250 on all teeth and a base line 252, with base line 252 being obtained from a digital model of the patient's jaw. Thus, with a plurality of gingival curves 250 and base line 252, a Hermite surface patch that represents gingival surface 251 can be generated. While a Hermite-Spline approach to generation of gingival curve 250 and gingival surface 251 is used in the exemplary embodiment, any other process for defining initial gingival curves along a line around a tooth (LAT) on a jaw within an interproximal area between two teeth and/or generation of gingival surfaces can be utilized.

Figure 2D:
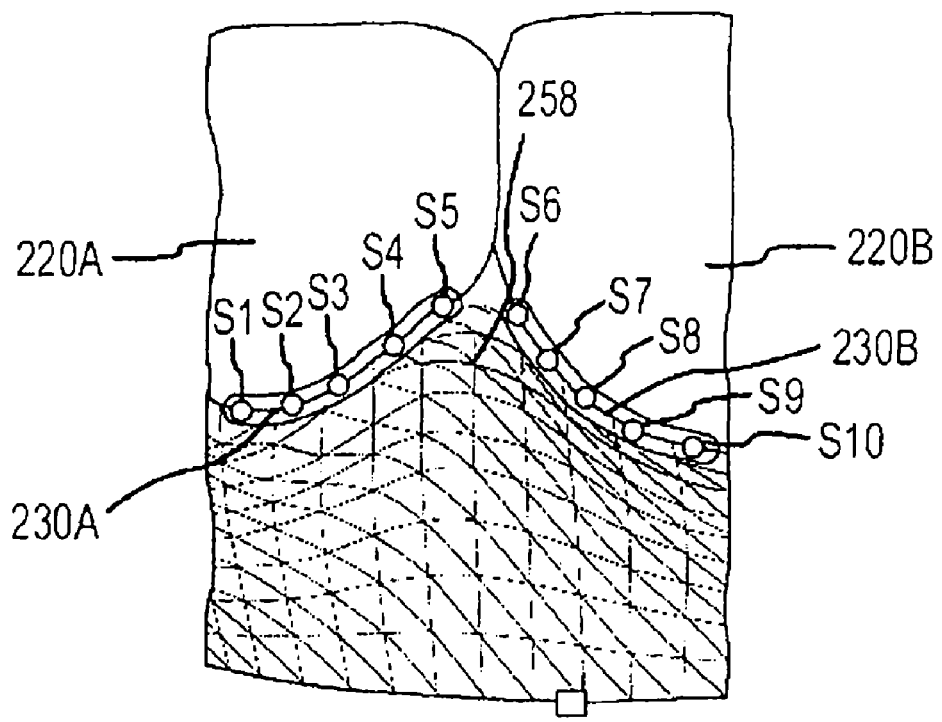
FIG. 2D illustrates a diagram of an exemplary interproximal area between two neighboring teeth, as a sampled points and a gingival parametric curve in accordance with an exemplary embodiment of the present invention.

Rather than having gingival curves 250 comprise a sharp point or other narrow region in the interproximal areas 258, as illustrated in FIG. 2D, that can cause weakening of the aligner material during use, the initial gingival curves 250 are replaced with a modified, dynamic cutting curve. In accordance with an exemplary embodiment, with reference to FIG. 2D, a modified curve can be generated to replace the initial gingival curves (104B) by initially obtaining a plurality of sample points, e.g., s1, s2 ... s9 and s10, from a pair of gingival curve portions 230A and 230B residing on each side of an interproximal area. Sample points s1-s10, are then converted into point lists with associated geometric information, for example, into ADF or other like data formats. In accordance with an exemplary embodiment, five sample points are collected from each of curve portions 230A and 230B; however, fewer or more sample points can also be collected. Sample points s5 and s6 are suitably selected proximate the inner region between two teeth, but sufficiently distanced from where the two teeth meet or come to a point or narrow region within interproximal area 258.

Figure 2E:
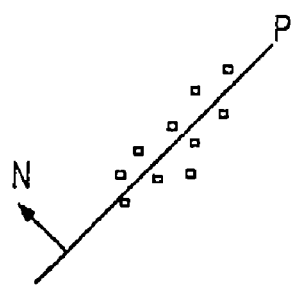
FIG. 2E illustrates a diagram of an average plane and its normal from the sample points derived from FIG. 2D in accordance with an exemplary embodiment of the present invention.
Figure 3:
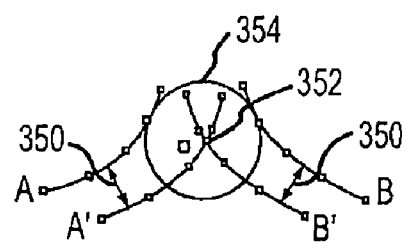
FIG. 3 illustrates a diagram and graphical representations of an exemplary method of projecting sample points and generation of a cylinder in accordance with an exemplary embodiment of the present invention.

Such a collection of sample points s1-s10 provide a plurality of points in space (not in the same plane) that can be used to generate an average plane and its normal. For example, with reference to FIG. 2E, an average plane (P) passing through ten points in space collected from sampled points s1-s10 can be generated, along with its normal (N). Sample points s1-s10 can then be projected onto plane (P) to generate two new curves, A and B as illustrated in FIG. 3, that are associated with gingival curve portions 230A and 230B.

To minimize weakening of a region of the aligner material within the interproximal area, the modified dynamic curve can be configured with an offset adjustment that comprises a minimum radius requirement in the interproximal area 258 (see FIG. 2D) to prevent breakage of the aligner material during use. As shown in FIG. 3, two parallel curves A' and B' can be defined with an offset adjustment 350 between curves A and B and parallel curves A' and B'. An intersection point 352 between parallel curves A' and B' is then generated. In accordance with an exemplary embodiment, offset adjustment 350 comprises approximately 3 mm, but can comprise longer or shorter values in other embodiments so long as an intersection point 352 is generated. In the event that an initial offset adjustment 350 does generate an intersection point 352, offset adjustment 350 can be suitably increased or decreased in increments, e.g., in 0.1 mm increments, until an intersection point 352 is found. Offset adjustment 350 is further configured to take into account that a resulting dynamic cutting curve should have sufficient radius in the interproximal area to facilitate enough resistance force applied to the teeth to cause effective movement, but not too small radius as to facilitate breakage, e.g., a sharp point or other narrow portion of material can create a stress region susceptible to break during use.

Figure 4:
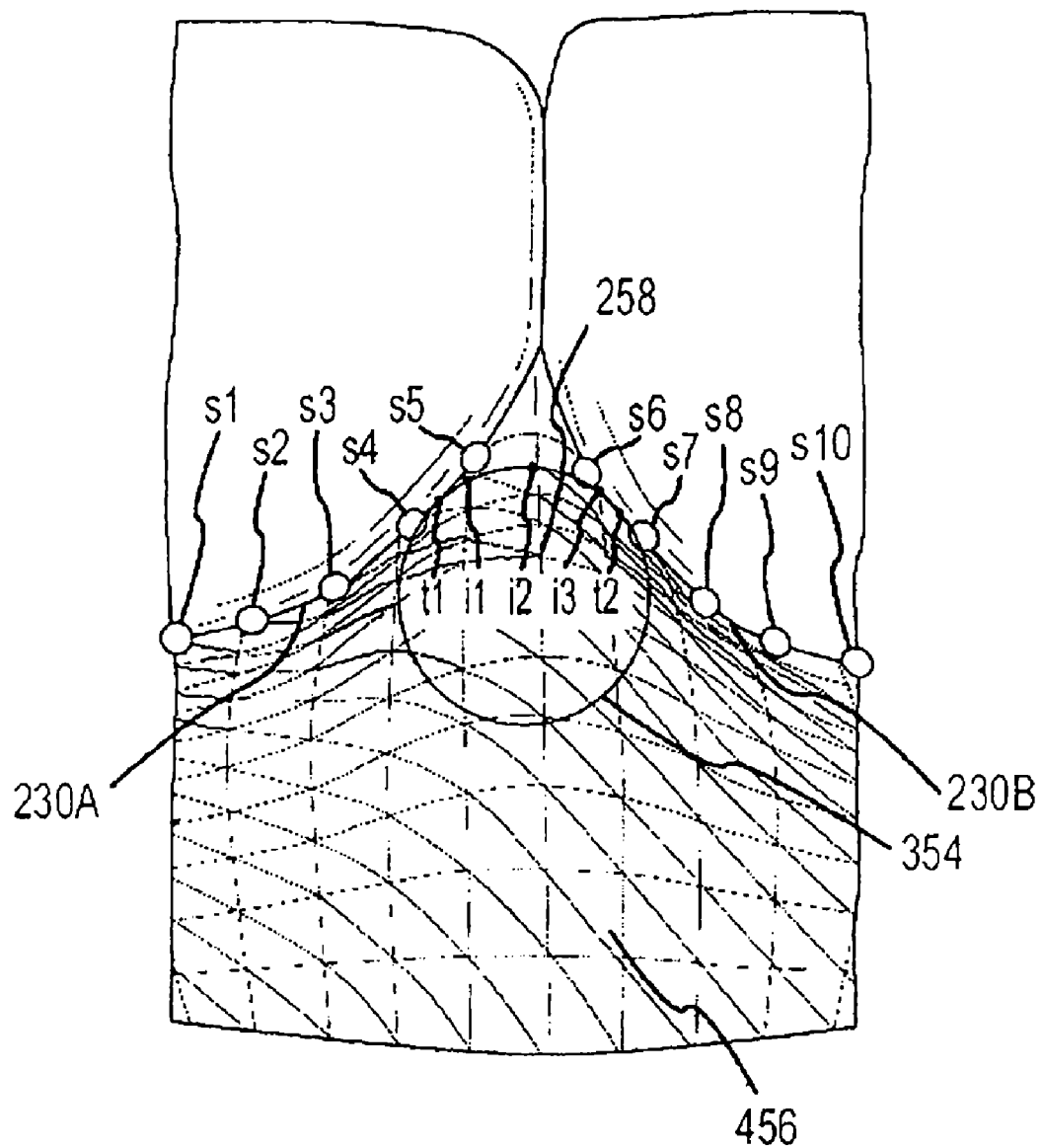
FIG. 4 illustrates a diagram and graphical representation of a dynamic cutting curve region in accordance with an exemplary embodiment of the present invention.

Next, a cylinder 354 with an axis at intersection point 352 and direction N, having a radius equal to offset adjustment 350, can be suitably generated. Cylinder 354 can then facilitate the defining of the modified gingival curve. For example, with reference to FIG. 4, tangent points t1 and t2 between cylinder 354 and curve portions 230A and 230B (defined by sample points s1, s2, ... s10) and intersection points i1, i2 and i3 between cylinder 354 and a plurality of gingival parametric curves 456 can be suitably defined to generate a dynamic cutting curve between teeth 220A and 220B (see FIG. 2D). Gingival parametric curves 456 can be suitably generated in various manners, for example, such as by use of the conventional Hermite surface patch process, or any other process for generating gingival parametric curves.

In addition, while two tangent points t1 and t2 and three intersection points i1, i2 and i3 are defined in the exemplary embodiment, additional or fewer points can also be utilized to generate the dynamic cutting curve between two teeth.

Accordingly, rather than have the cutting curve comprise a sharp point or other narrow region, a plurality of intersection points, such as i1, i2 and i3, and tangent points t1 and t2, are used to generate a dynamic cutting curve in the interproximal region. For example, the dynamic cutting curve illustrated in FIG. 4 can be defined as the curve passing through sample points s1-s4, then tangent point t1, intersection points i1-i3, tangent point t2, and then sample points s7-s10.

Such a process for defining a dynamic cutting curve between two teeth can then be suitably applied to the interproximal regions of other teeth within a patient, with the complete dynamic cutting curve then being output for conversion into machine executable code to facilitate cutting of the aligner material (106B) (see FIG. 1B).

Figure 5:
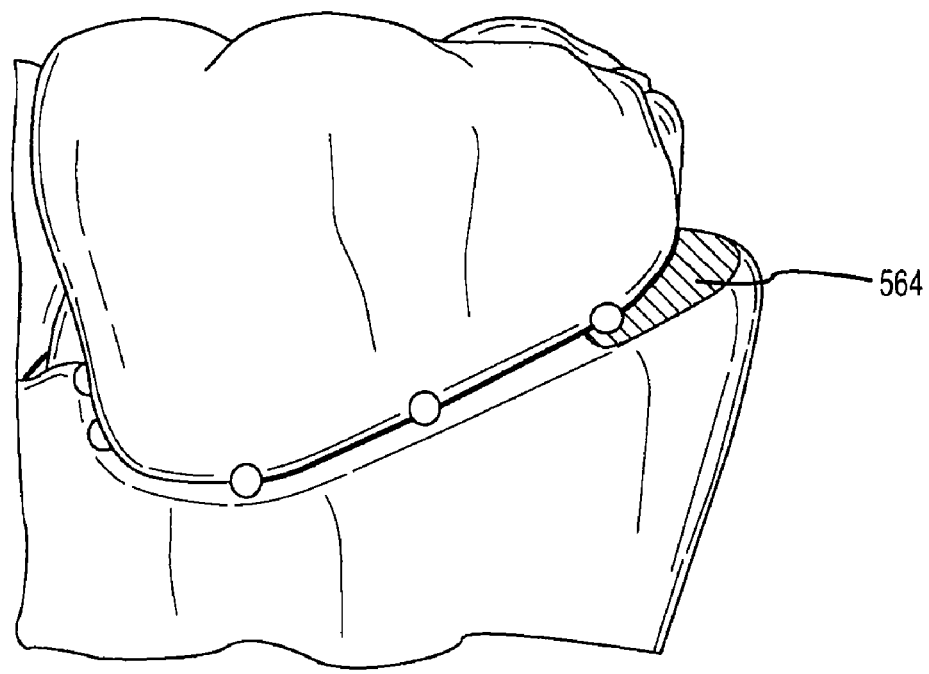
FIGS. 5-7D illustrate a diagrams of a back molar region and lifting of a dynamic cutting curve in accordance with an exemplary embodiment of the present invention.

The above process for defining the dynamic cutting curve is particularly suitable in the regions between two teeth, for example, in the labial sides of a jaw of the patient. In the back molar region of a patient, where the dynamic cutting curve is originally defined as the LAT of a back molar, extraneous aligner material can sometimes result. For example, with reference to FIG. 5, extraneous aligner material can be left within a region 564 that can result in pain or discomfort to a patient if the aligner material is left in its original unmodified configuration, and thus has to be manually removed or cut under conventional processes. However, with reference again to FIG. 1B, in accordance with another exemplary embodiment, computer-implemented method 100 can also be configured to further modify the dynamic curves in the back molar areas (108B), such as illustrated in FIG. 6, prior to being output for conversion into machine executable code to facilitate cutting of the aligner material (106B) by lifting the dynamic curve within the region proximate the back molars.

Figure 7A:
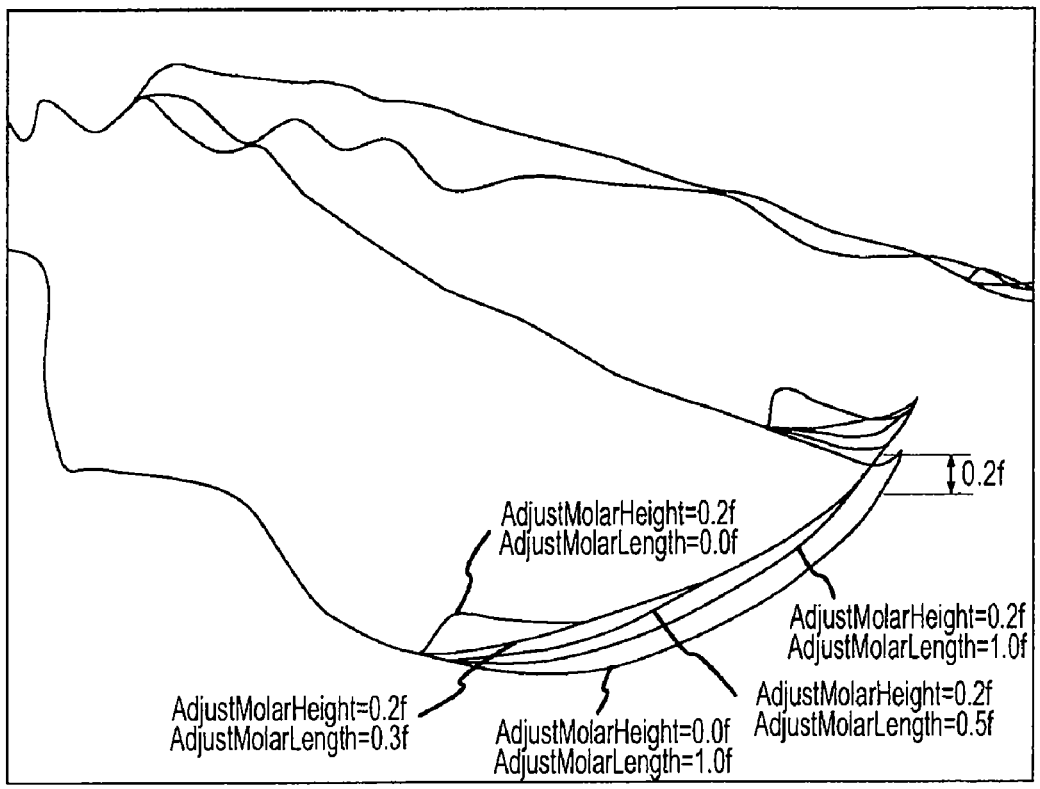

For example, the dynamic cutting curve can be lifted by an adjustment based on at least one of two input parameters, including an adjustment of a molar height parameter (AdjustMolarHeight or AMH) and/or an adjustment of a molar length parameter (AdjustMolarLength or AML), as illustrated in FIG. 7A. In adjusting based on the molar height parameter AMH, the dynamic curve is raised up to just above the crown surface of the molar, with an adjustment between approximately 1.0 mm and 3 mm being used, e.g., the dynamic curve being lifted an average of approximately 1.5 mm. In addition, the molar length parameter AML can also be adjusted, wherein parameter AML controls the area where the curve is adjusted gradually, i.e., along the length of the curve for example, and wherein parameter AML can vary from a unit length (AML=1) to shorter length/areas thereof.

Figure 7B:
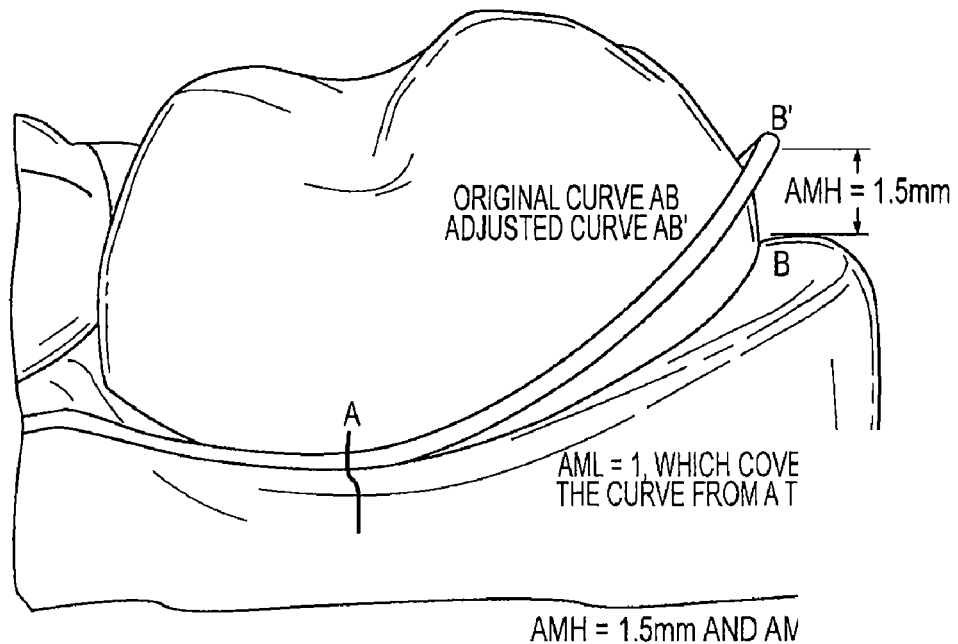
Figure 7C:
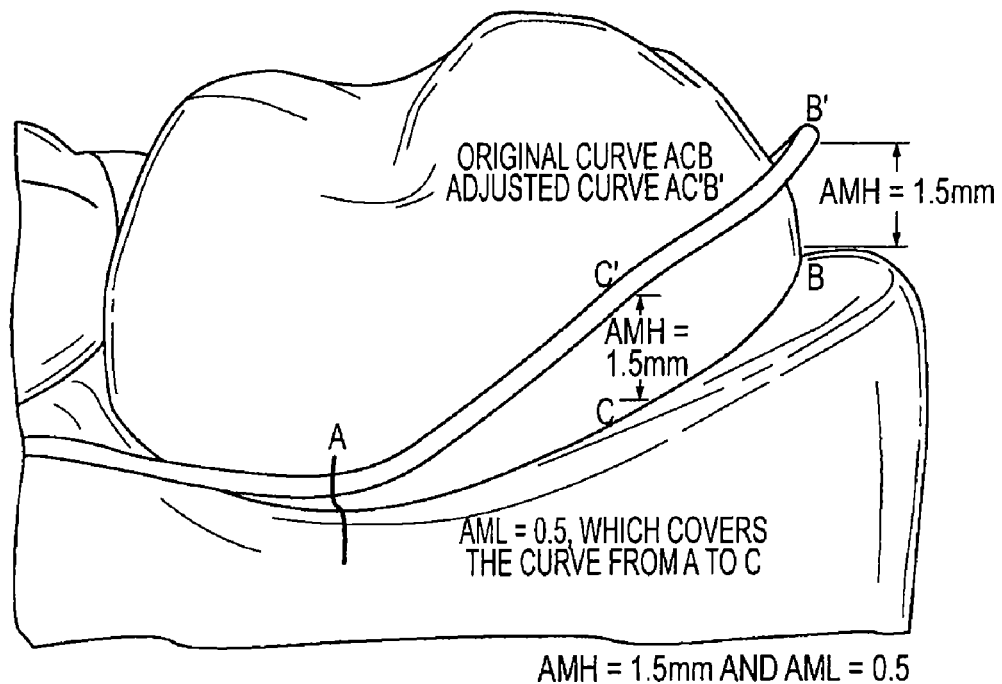
Figure 7D:
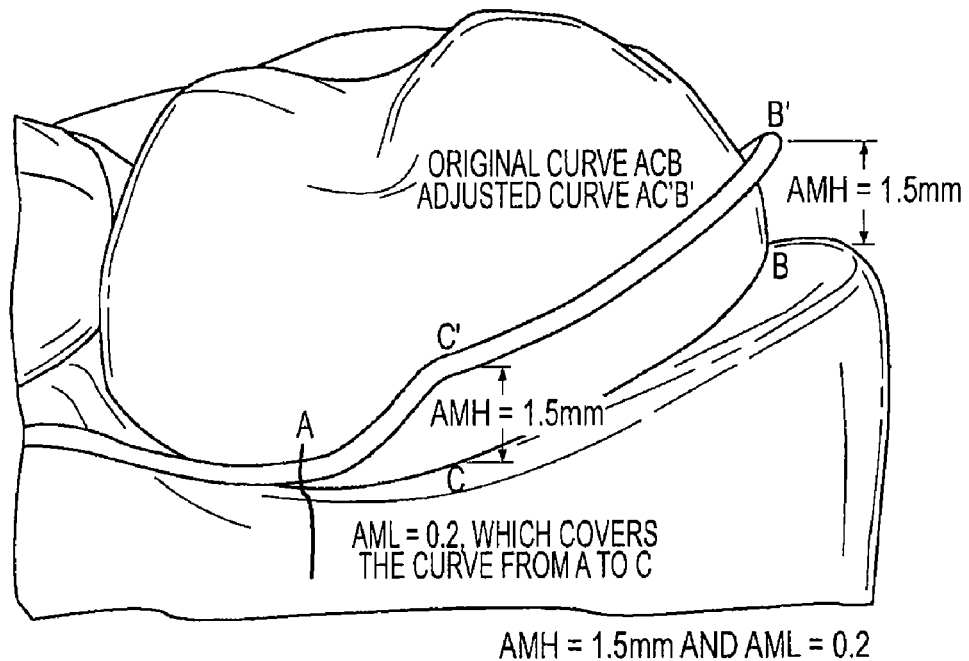
Figure 8:
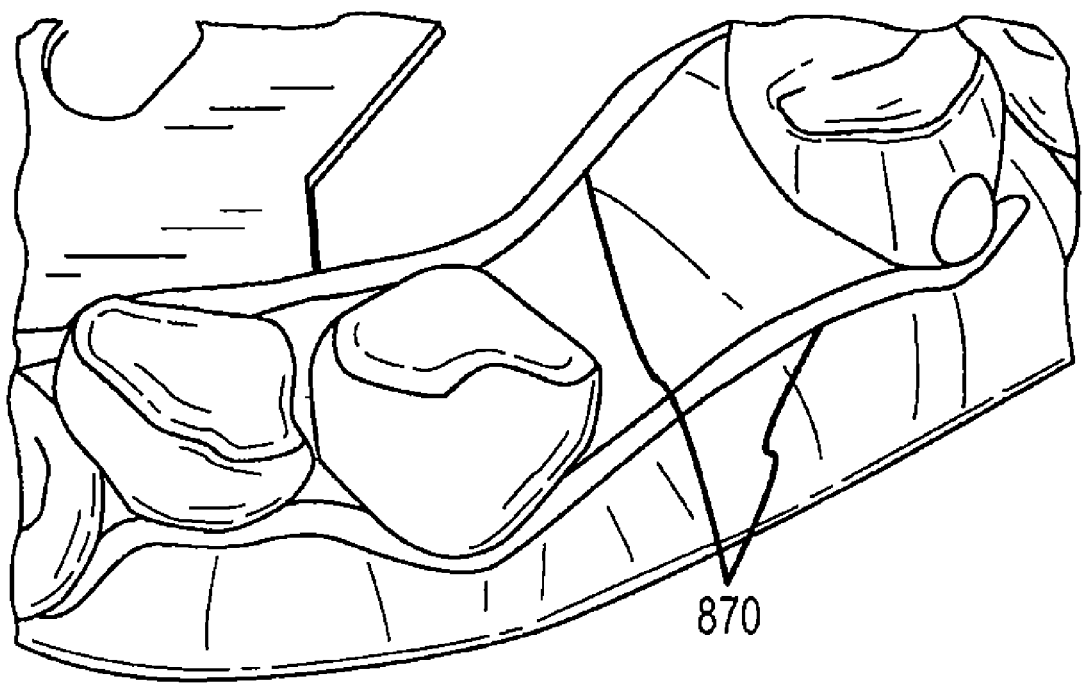
FIG. 8 illustrates a cutting curve without a pontic object in accordance with an exemplary embodiment of the present invention.

For example, with reference to FIG. 7B, in the case where the dynamic cutting curve can be adjusted from point A to B, the parameter AML=1, this means the curve from A to B is lifted gradually with the largest height/lift value (AMH=1.5 mm) at the point B (lifting the curve from B up to B'). In another example, with reference to FIG. 7C and with AML=0.5, the dynamic cutting curve portion from A to C is lifted gradually, and the dynamic cutting curve portion from C' to B' parallels that of the curve portion from C to B (comprise an AMH=1.5 mm). Further, with reference to FIG. 7D and with AML=0.2, the dynamic cutting curve portion from A to C is lifted rapidly (to an AMH=1.5 mm), with the dynamic cutting curve portion from C' to B' thereafter parallel to that of the curve from C to B. Various other values of parameter AML can also be selected to generate additional "lifted" dynamic cutting curves. The selection of parameters AML and AMH is determined by selecting suitably smooth curves that will allow the aligner material to be configured along the teeth to provide sufficient force for teeth movement and yet avoid the discomfort in the back molar region. Thus, in the above examples, the adjusted/lifted cutting curve in FIG. 7D may not be selected in many instances, instead having the adjusted curves similar to those illustrated in FIGS. 7B and 7C utilized.

Figure 6:
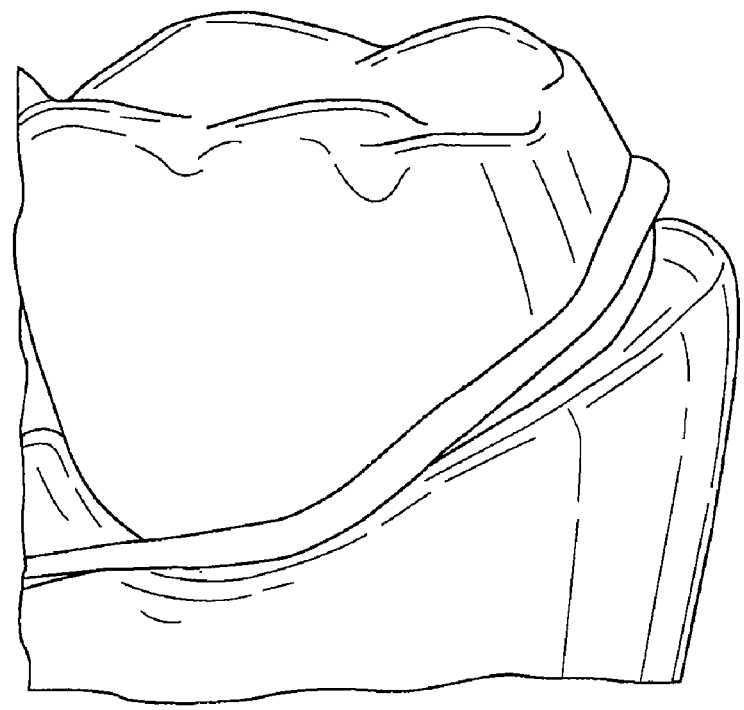

As a result of the adjustment of the dynamic cutting curve through the use of lifting parameters AMH and AML, the dynamic cutting curve can be suitably lifted proximate the back molar area, such as illustrated in FIG. 6. Such an adjustment can allow the aligner material to be configured along the teeth to provide sufficient force for teeth movement and yet avoid the discomfort in the back molar region.

Figure 9:
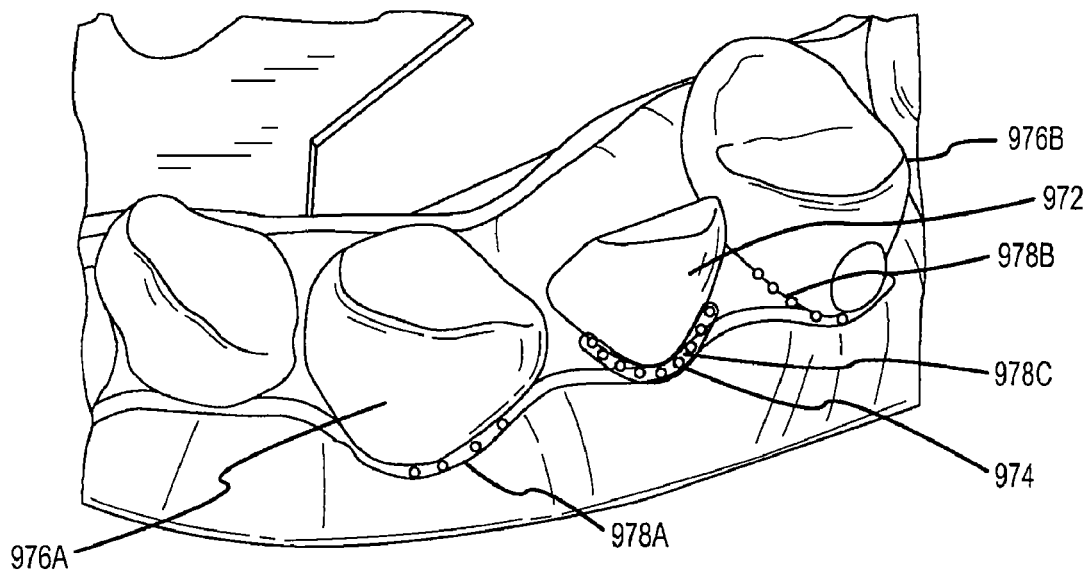
FIG. 9 illustrates a dynamic cutting curve configured with a pontic object in accordance with an exemplary embodiment of the present invention.

In accordance with another exemplary embodiment, method 100B can also comprise the automated generation of dynamic cutting curves within a pontic region of a patient as illustrated in FIG. 9. Pontic objects 972 are placed in locations where two neighboring teeth have a large gap, such as when a tooth has previously been removed. A pontic object comprises a virtual tooth configured to fill in the gap, typically within the labial side of the aligner. Methodologies for generating pontic objects are known in the art, but such conventional methodologies do not take into account the use of pontic objects when generating the cutting curves and thus require manual trimming of pontic cases. However, in accordance with this exemplary embodiment that includes a pontic object, the dynamic cutting curve can be suitably configured as if the pontic object comprised a real tooth, utilizing the techniques disclosed herein to facilitate a suitable cutting curve.

To generate a dynamic cutting curve configured to address such large gaps, with continued reference to FIG. 9, a pontic object 972 is first generated by any conventional methods for generating such pontic objects. Next, a gingival curve 974 is generated around pontic object 972 on the gingival surface. Pontic object 972 and neighboring teeth 976A and 976B define two virtual interproximal areas A and B. Similar to the generation of curve portions 230A and 230B of FIG. 2, curve portions 978A, 978B and 978C can be suitably generated. For example, the collection of sample points s1, s2, ... sn along the gingival curves of pontic object 972 and teeth 976A and 976B, the generation of average planes (P) and normals (N), and the generation of parallel lines and an intersection point to provide a cylinder like that illustrated in cylinder 354 in FIG. 3 and FIG. 4, can be conducted to define a plurality of tangent points t1, t2, ... tn and intersection points i1, i2, i3 ... in within interproximal regions A and B of FIG. 9. As a result, a further modified dynamic cutting curve configured to address pontic objects can be defined.

Figure 10:
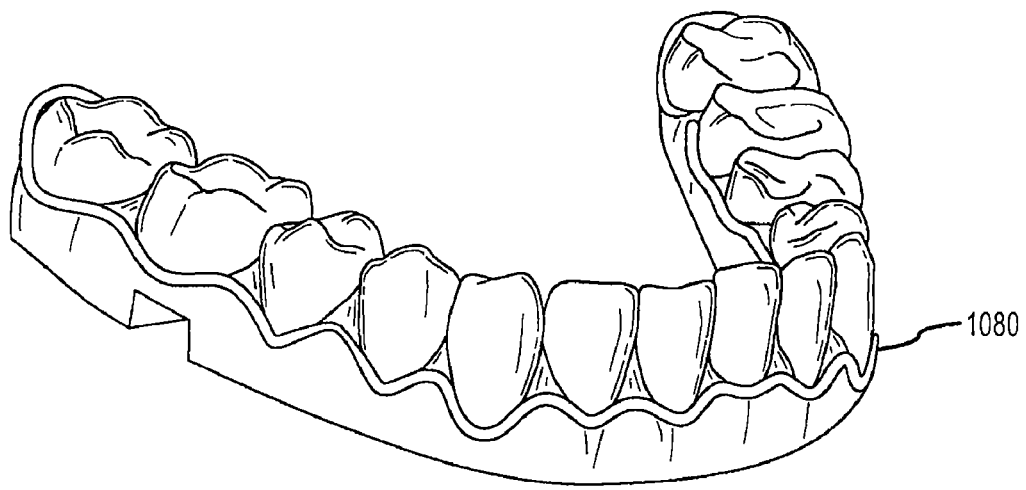
FIG. 10 illustrates an exemplary complete dynamic cutting curve in accordance with an exemplary embodiment of the present invention.

The dynamic cutting curve can be suitably generated for each of other the teeth and interproximal areas between those teeth, with or without adjustments for back molar regions and/or pontic objects, for both the labial and lingual side of a patients teeth. As a result of generating dynamic cutting curve portions within the various interproximal areas between teeth of a patient, a complete or whole dynamic cutting curve 1080 can be suitably generated, such as that illustrated in FIG. 10.

After generation of the complete dynamic cutting curve 1080 for each of other the teeth and interproximal areas between those teeth, dynamic cutting curve 1080 can then be output for conversion into machine executable code to facilitate cutting of the aligner (106B). For example, in an exemplary embodiment, dynamic cutting curve 1080 can be converted into a GCode or other standard machine executable code used in CNC cutting machines, such as that disclosed in U.S. Pat. No. 7,040,896, entitled "Systems and Methods for Removing Gingiva From Computer Tooth Models" or other like methodologies.

Figure 11:
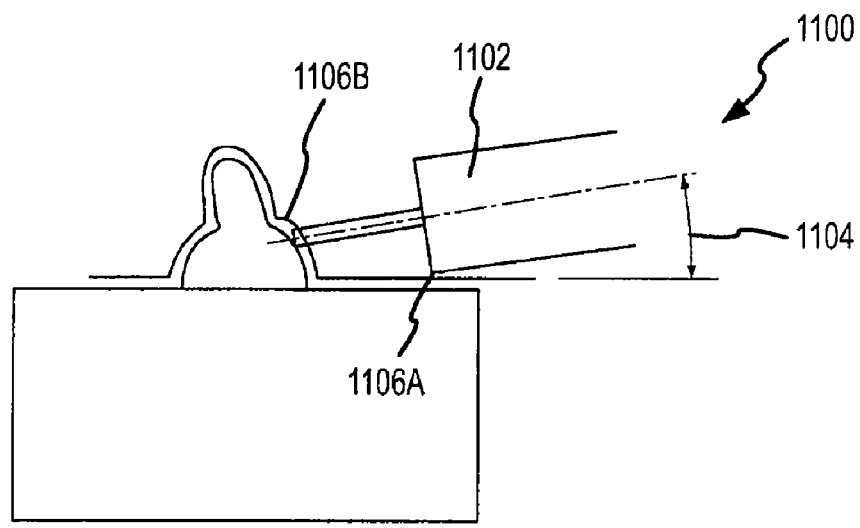
FIG. 11 illustrates a diagram for a cutting tool and fixture in which collision can occur in accordance with an exemplary embodiment of the present invention.

As discussed, conventional methods for generating cutting curves do not suitably address the potential for collisions of a cutting tool within the cutting machine when cutting the aligner material from the SLA molds. For example, with reference to FIG. 11, a cutting tool 1102 can potentially collide with the mold and aligner material during the cutting process, particularly if the cutting angle is not suitably controlled. For example, a cutting angle 1104 cannot be too small or cutting tool 1102 can potentially collide with a fixture 1106A during cutting, but also cannot be too large so as to potentially collide with an upper exterior side 1106B. However, in accordance with another aspect of the present invention, a method for dynamic adjustment of the cutting tool along the dynamic cutting curve can be provided. In accordance with an exemplary embodiment, with reference to FIG. 12, a plurality of cutting areas around the dynamic cutting curve are provided, including a labial cutting area 1202, a lingual cutting area 1204, back molar cutting areas 1206A and 1206B, as well as four transition zones 1208 located between areas 1202 and 1206A, areas 1206A and 1204, areas 1204 and 1206B, and areas 1206B and 1202. Within such areas 1202, 1204, 1206A and 1206B and zones 1208, the method for dynamic adjustment of the cutting tool is configured to suitably adjust cutting angle 1104 to avoid collisions.

For example, in accordance with an exemplary embodiment, cutting angle 1104 is adjusted to approximately 15 degrees within labial area 1202, to approximately 35 degrees within lingual areas 1204, and approximately 40 degrees within back molar areas 1206A and 1206B. By approximate adjustment, within about ±1.5 degrees is suitable, although a greater range can also be realized, e.g., ±5 degrees or more. Transition areas 1208 are suitably to facilitate a gradual transition from one cutting area to another cutting area, increasing and/or decreasing cutting angle 1104. For example, as cutting tool 1102 proceeds in a clockwise fashion from an approximate cutting angle of 15 degrees within labial cutting area 1202 to an approximate cutting angle of 40 degrees for back molar cutting area 1206A, a transition zone 1208 in between will gradually increase cutting angle 1104 from approximately 15 degrees to approximately 40 degrees.

Figure 12:
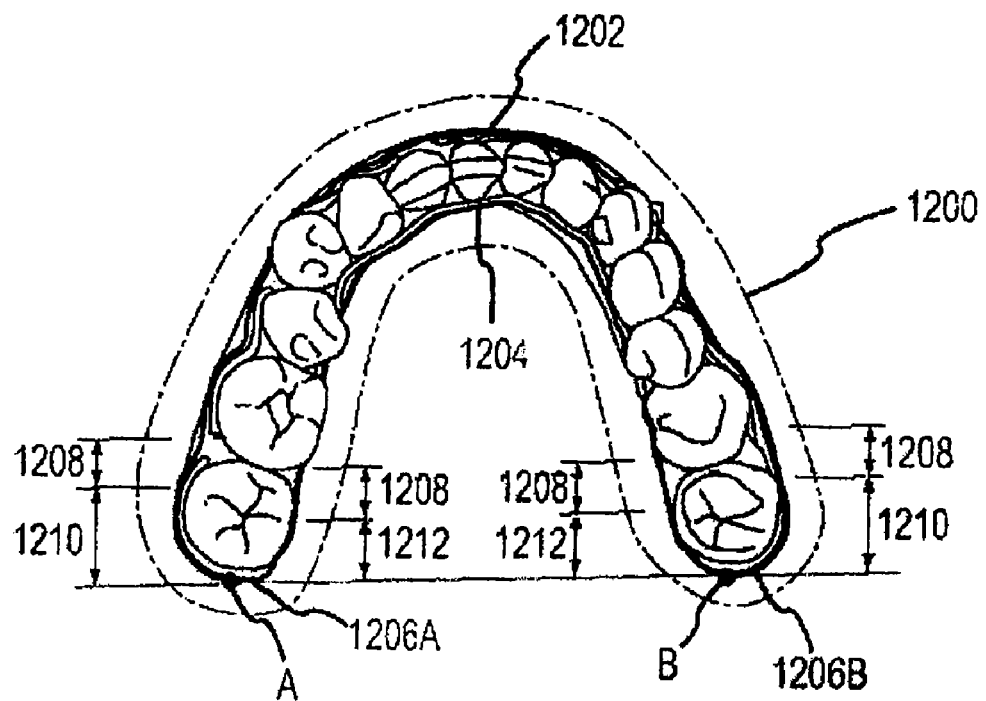
FIG. 12 illustrates a diagram for adjusted cutting areas in accordance with an exemplary embodiment of the present invention.

To define where areas 1202, 1204, 1206A and 1206B and zones 1208 start and end, with continued reference to FIG. 12, additional parameters such as an angle begin 1210 and an angle end 1212 can be provided. Angle begin 1210, angle end 1212 and transition zones 1208 can comprise float values that are configured to control cutting angle boundaries. Thus, for example as illustrated in FIG. 12, with a reference line drawn from point A to point B that is tangent with the cutting curve in back molar regions, a parallel line can be generated, with that parallel line being spaced a distance equal to the float value of angle begin parameter 1210 and angle end parameter 1212. Thus, for example, for float values of approximately 3 mm for angle begin parameter 1210 and angle end parameter 1212, the locations where the parallel line intersect the length along the cutting curve can suitably define where the cutting areas for back molar regions 1206A and 1206B start and end. Transition zones 1208 are defined by floating values that comprise an additional distance from that parallel line. Thus, for a floating value of approximately 1 mm for transition zones 1208 (that would provide a distance of approximately 4 mm from the tangent line from A to B), the beginning and end of such transition zones can be established, as well as labial and lingual cutting areas 1202 and 1204.

The floating values for angle begin parameter 1210, angle end parameter 1212 and transition zones 1208 can comprise various values. For example, parameters 1210 and 1212 can comprise the same values, or different values, depending on the desired length of back molar cutting areas 1206A and 1206B, as well as when the desired position to start and end such cutting areas. In addition, transition zones 1208 can also comprise the same value, or can comprise different values, again depending on the desired length of labial and lingual cutting areas 1202 and 1204. For example, such starting and ending positions and length can suitably depend upon the diameter and/or settings of the cutting tool.

Figure 13:
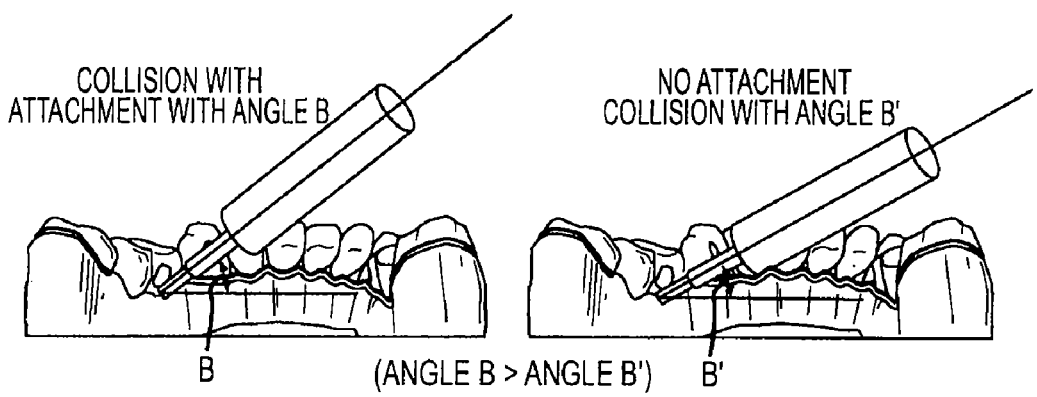
FIG. 13 illustrates diagrams for a cutting tool and attachment with and without adjustment of the cutting angles in accordance with an exemplary embodiment of the present invention.

Accordingly, with reference to FIG. 13, an example of an uncontrolled cutting angle B within the labial cutting area that is substantially greater than a controlled cutting angle B', for example having a cutting angle of approximately 15 degrees, can result in collision between the cutting tool and the aligner material, whereas the controlled cutting angle B' avoids collision.

Figure 14:
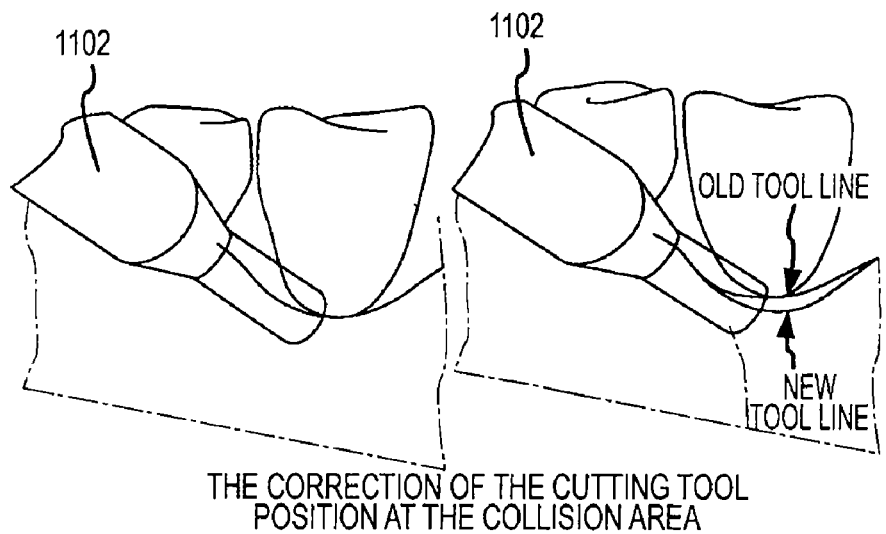
FIGS. 14 and 15 illustrate diagrams for adjustment of the cutting tool in accordance with exemplary embodiments of the present invention.
Figure 15:
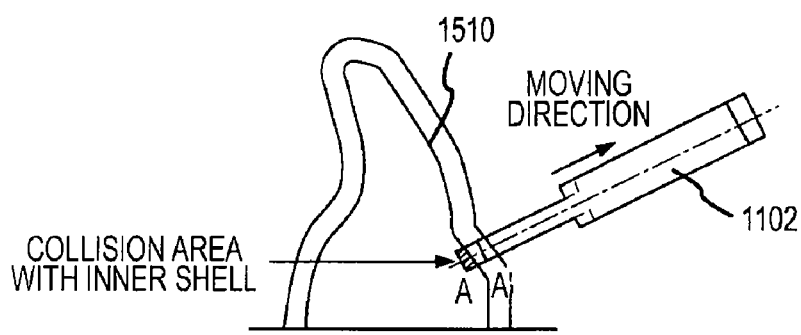

In accordance with another exemplary embodiment, the method for dynamic adjustment of the cutting tool can also be configured to automatically adjust cutting tool 1102 a specified distance away from the initial cutting tool line, such as moving cutting tool 1102 low as illustrated in FIG. 14 to avoid collision with the teeth or attachment device, and/or away from an inner shell 1510 along the cutting tool axis to avoid collision with inner shell 1510 as illustrated in FIG. 15.

To avoid collision with the teeth or attachment device by moving the cutting tool low, a determination is made as to whether collision with the teeth or attachment device will occur, followed by adjustment of cutting tool 1102 in very small increments from an old tool line to a new tool line, such as increments of approximately 0.01 mm. Such adjustment is continued until the collision with the teeth or attachment device is eliminated or a maximum value of adjustment, e.g., 0.2 mm, is reached. In addition, the determination of collision with the teeth or attachment device and the incremental adjustment process is continuously repeated while moving cutting tool 1102 along the cutting curve. Thus, for example, while cutting tool 1102 may be adjusted approximately 0.04 mm at one point along the cutting curve, at another point along the cutting curve an adjustment of 0.08 mm of the position of cutting tool 1102 may be needed to avoid collision. Further, although adjacent points along the cutting curve may require very different amounts of adjustment, in accordance with an exemplary embodiment, these required amount of adjustments may be suitably modified even further to provide a smooth transition of cutting tool 1102 without collision with the teeth or attachment device as it moves along the cutting curve.

To avoid collision with inner shell 1510 at a position A, a determination is made as to whether collision with inner shell 1510 will occur, followed by automatically adjusting cutting tool 1102 away from inner shell 1510 in very small increments, e.g., in increments of approximately 0.01 mm, until collision with the inner shell is eliminated at a new position A'. Similar to the process above, the determination of collision with inner shell 1510 and the incremental adjustment process away from inner shell 1510 is continuously repeated while cutting tool 1102 is moved or transitioned along the cutting curve. Thus, for example, while cutting tool 1102 may be adjusted way from inner shell 1510 by approximately 0.04 mm at one point along the cutting curve, at another point along the cutting curve an adjustment away from inner shell 1510 of approximately 0.08 mm may be needed to avoid collision. Further, although adjacent points along the cutting curve may require very different amounts of adjustment away from inner shell 1510, in accordance with an exemplary embodiment, these required amounts of adjustment may be suitably modified even further to provide a smooth transition of cutting tool 1102 as it moves along the cutting curve without collision with inner shell 1510.

Figure 16:
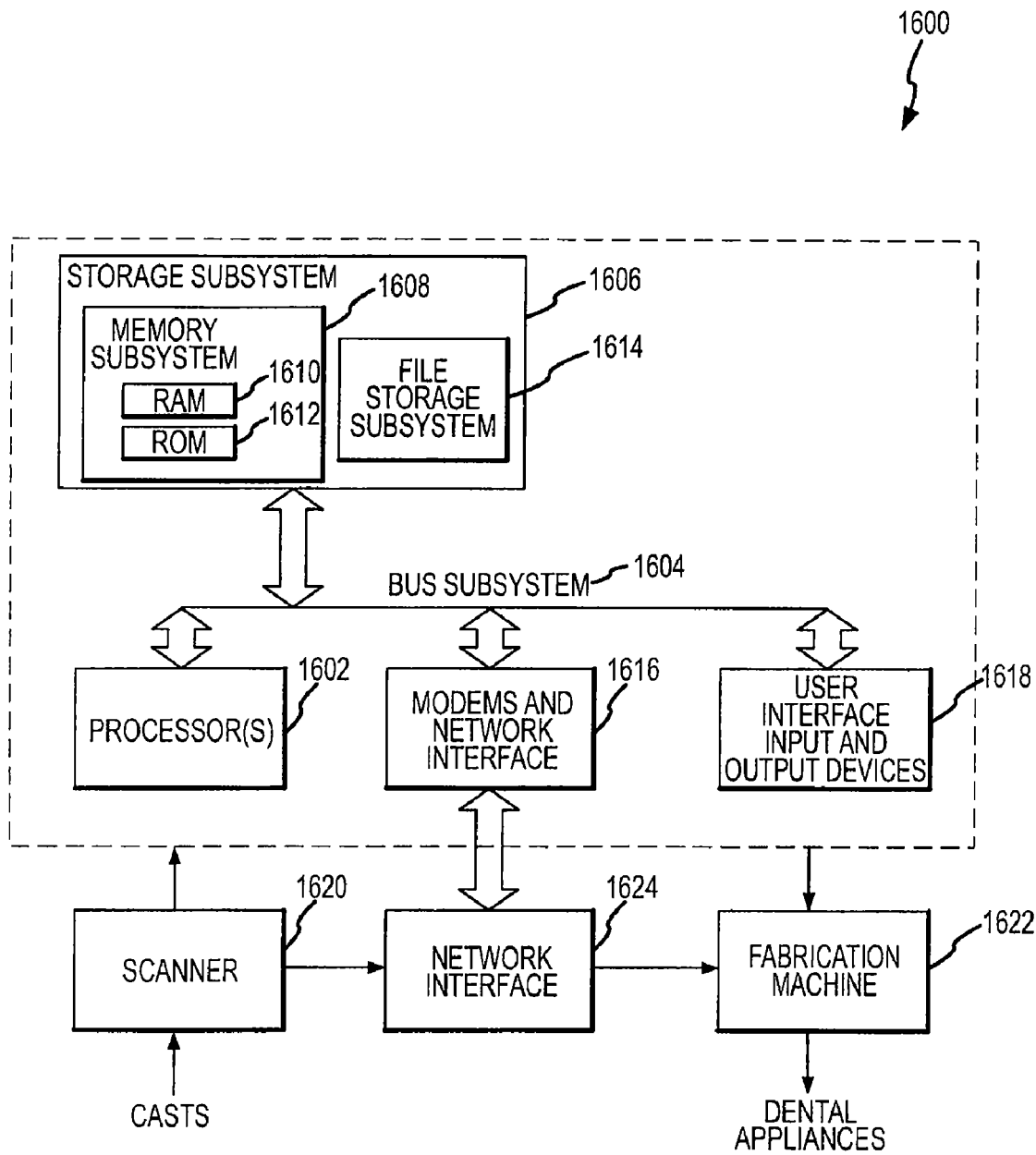
FIG. 16 illustrates a block diagram for control system for facilitating automated generation of the dynamic cutting curve and/or for dynamic adjustment of the cutting tool in accordance with an exemplary embodiment of the present invention.

Such automated generation of the dynamic cutting curve and/or for dynamic adjustment of the cutting tool can be conducted with one or more computer-based systems through the use of one or more algorithms. For example, with reference to FIG. 16, an exemplary computerized system 1600 for facilitating automated generation of the dynamic cutting curve and/or for dynamic adjustment of the cutting tool can comprise one or more computer-based systems or modules, microprocessors, memory systems and/or input/output devices for processing data and information, comprising one or more software algorithms configured for computing and/or performing other functions set forth herein. For example, exemplary computerized system 1600 can comprise memory or storage subsystems 1606-1614, processors 1602, network interfaces 1616, input/output devices 1618 and/or other components 1620-1624 as disclosed in U.S. Pat. No. 7,040,896, entitled "Systems and Methods for Removing Gingiva From Computer Tooth Models", and assigned to Align Technology, Inc., or any other computerized system components used for computational orthodontics.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the component and methodologies and/or steps may be deleted, modified, or combined with other components, methodologies and/or steps, depending on the whether the application is for orthodontic, dental, medical or other treatment or therapeutic contexts. Moreover, it is understood that various of the methods and steps disclosed herein, such as generating of IDDS, identifying or gingival curves or other processes can also comprise any other conventional techniques, or any later developed techniques, for facilitating such methods and steps. These and other functions, methods, changes or modifications are intended to be included within the scope of the present invention, as set forth in the following claims.

The invention claimed is:

1. A computer-implemented method for automated generating of a cutting curve on a gingival surface to facilitate cutting of an aligner material, said computer-implemented method comprising:
   generating a digital data format that defines initial gingival curves along teeth on a jaw structure of a patient within an interproximal area between two teeth;
   converting the digital data format that defines the initial gingival curves into a plurality of points with geometric information associated with a first pair of gingival curve portions of the initial gingival curves residing on each side of the interproximal area;
   generating a digital data format that defines a dynamic cutting curve within the interproximal area that is made to fit through at least a portion of the plurality of points with geometric information; and
   converting in a microprocessor the digital data format that defines the dynamic cutting curve into machine executable code for cutting of the aligner material.

2. The computer-implemented method according claim 1, further comprising providing an offset adjustment configured to minimize weakening of a region of the aligner material within the interproximal area.

3. The computer-implemented method according to claim 2, wherein said converting the digital data format that defines the initial gingival curves into a plurality of points with geometric information associated with a first pair of gingival curve portions of the initial gingival curves residing on each side of the interproximal area comprises:
   defining an average plane and its normal in three-dimensional space based on a sample of said plurality of points;
   projecting two groups of sample points on said average plane associated with said gingival curve portions;
   defining a second pair of curve portions in parallel with said gingival curve portions with a predetermined offset comprising a minimum radius requirement in the interproximal area of the aligner material;
   finding an intersection point between said second pair of curve portions and generating a cylinder having a radius comprising said predetermined offset;
   finding tangent points between said cylinder and said sample of points associated with said first pair of curve portions; and
   defining said dynamic cutting curve within the interproximal area based on said sample of points, said intersection point and tangent points.

4. The computer-implemented method according to claim 1, further comprising modifying said dynamic cutting curve in a back molar area to remove extraneous aligner material.

5. The computer-implemented method according to claim 4, wherein said modifying said dynamic cutting curve in said back molar area by adjustment of a length parameter and a height parameter associated with said dynamic cutting curve to proximately below a crown surface.

6. The computer-implemented method according to claim 5, wherein said modifying said dynamic cutting curve in said back molar area by adjustment of a length parameter and a height parameter comprises gradually lifting of said dynamic cutting curve to a first height along a first length portion, and then minimally lifting of said dynamic cutting curve along a second length portion.

7. The computer-implemented method according to claim 1, wherein said method further comprises automatically generating the dynamic cutting curve along a area around a pontic object between two teeth.

8. The computer-implemented method according to claim 7, wherein said method comprises automatically generating a cutting curve region around the pontic object on a gingival surface in a labial region.

9. The computer-implemented method according to claim 8, wherein said automatically generating a cutting curve region around the pontic object comprises finding intersection points between a gingival surface and a pontic object and then creating a modified dynamic curve region within two interproximal areas defined by the two teeth adjacent to the pontic object.

10. The computer-implemented method according to claim 1, wherein said creating the digital data format that defines the initial gingival curve and generating the digital data format that defines the dynamic cutting curve is conducted along an area around a pontic object between two teeth.

11. The computer-implemented method according to claim 1, wherein said method is further configured to avoid collision of a cutting tool with teeth, an attachment, an inner shell or a fixture when cutting the aligner material, and said method further comprises:
   generating a first cutting angle in a labial cutting area along said dynamic cutting curve;
   generating a second cutting angle in a lingual cutting area along said dynamic cutting curve; and
   generating a third cutting angle in a back molar cutting area along said dynamic cutting curve.

12. The computer-implemented method according to claim 11, further comprising generating transition zones between said labial cutting area and said back molar cutting area, and between said lingual cutting area and said back molar cutting areas.

13. The computer-implemented method according to claim 11, wherein the first cutting angle is approximately 15 degrees in the labial cutting area; the second cutting angle is approximately 35 degrees in the lingual cutting area; and the third cutting angle is approximately 40 degrees in the back molar cutting area.

14. A computer-implemented method for automated generating of a cutting curve on a gingival surface to facilitate cutting of an aligner material, said computer-implemented method comprising:
generating an initial gingival curve within an interproximal area between two teeth;
replacing said initial gingival curve with a modified portion to generate a dynamic cutting curve;
outputting said dynamic cutting curve for conversion into machine executable code for cutting of the aligner material; and
automatically adjusting a cutting tool away from an initial cutting tool line and away from an inner shell along a cutting tool axis to avoid collision of the cutting tool with teeth, an attachment device, an inner shell or a fixture when cutting the aligner material.

15. The computer-implemented method according claim 14, wherein said automatically adjusting the cutting tool away comprises incrementally adjusting the cutting tool based on defined increment values from said dynamic cutting curve until collision with at least one of the teeth and the attachment device is eliminated or a maximum adjustment value is reached.

16. The computer-implemented method according claim 14, wherein said automatically adjusting the cutting tool away comprises incrementally adjusting the cutting tool away from the inner shell in defined increment values until collision with the inner shell is eliminated.

17. A computerized system for automatic generation of a cutting curve on a gingival surface to facilitate cutting of an aligner material, said computerized system comprising:
a microprocessor; and
a data storage device including a plurality of algorithms; the microprocessor configured by the algorithms to:
generate a plurality of gingival parametric curves within an interproximal area between two teeth representing a gingival surface;
convert a digital data format that defines initial gingival curves along teeth on jaw structure of a patient into a plurality of points disposed on each side of the interproximal area;
project a sample of the plurality of points on to a plane in three-dimensional space which passes through an average of the sample of the plurality of points to generate a second pair of curved portions;
generate a third pair of curve portions having a predetermined offset from the second pair of curved portions including an intersection point and a minimum radius in the interproximal area;
determine tangent points between a cylinder having an axis at the intersection point and a radius equal to the predetermined offset and the sample of plurality of points and cylinder intersection points between the cylinder and a portion of the gingival parametric curves; and
generate a digital data format that defines a dynamic cutting curve within the interproximal area that is made to fit through at least a portion of the sample of plurality of points, the cylinder intersection points and the tangent points.

18. The computerized system according to claim 17, wherein the microprocessor is further configured to modify the dynamic cutting curve in a back molar area to remove extraneous aligner material.

19. The computerized system according to claim 17, wherein the microprocessor is further configured to generate the digital data format that defines the initial gingival curves and generate the digital data format that defines the dynamic cutting curve along an area around a pontic object between two teeth.

20. The computerized system according to claim 17, wherein the microprocessor is further configured to generate a first cutting angle in a labial cutting area along said dynamic cutting curve; generate a second cutting angle in a lingual cutting area along said dynamic cutting curve; and generate third cutting angle in a back molar cutting area along said dynamic cutting curve.

21. The computerized system according to claim 20, wherein the microprocessor is further configured to generate transition zones between said labial cutting area and said back molar cutting area, and between said lingual cutting area and said back molar cutting areas.

22. The computerized system according to according claim 17, wherein the microprocessor is further configured to automatically adjust a cutting tool in incremental defined values for avoiding collision of the cutting tool with at least one of teeth, an attachment device, an inner shell and a fixture when cutting the aligner material.

23. The computerized system according to claim 17, wherein the microprocessor is further configured to convert the digital data format that defines the dynamic cutting curve into machine executable code for cutting of the aligner material.

24. A computer-implemented method for automated generating of a cutting curve on a gingival surface to facilitate cutting of an aligner material, said computer-implemented method comprising:
generating a digital data format that defines initial gingival curves along teeth on a jaw structure of a patient and a plurality of gingival parametric curves within an interproximal area between two teeth and converting the digital data format that defines the initial gingival curves into a plurality of points with geometric information associated with a first pair of gingival curve portions of the initial gingival curves residing on each side of the interproximal area;
generating an average plane in three-dimensional space which passes through an average of a sample of the plurality of points, projecting the sample of the plurality of points on to the average plane to generate a second pair of curved portions, generating a third pair of curve portions having a predetermined offset from the second pair of curved portions including an intersection point and a minimum radius in the interproximal area, generating a digital data format that defines cylinder having an axis at the intersection point and a radius equal to the predetermined offset, determining tangent points between the cylinder and the sample of plurality of points and cylinder intersection points between the cylinder and a portion of the gingival parametric curves; and
generating a digital data format that defines a dynamic cutting curve within the interproximal area that is made to fit through at least a portion of the sample of plurality of points, the cylinder intersection points and the tangent points; and
converting in a microprocessor the digital data format that defines the dynamic cutting curve into machine executable code for cutting of the aligner material.

* * * * *